US006589213B2

(12) United States Patent
Reydel

(10) Patent No.: US 6,589,213 B2
(45) Date of Patent: *Jul. 8, 2003

(54) BODY CANAL INTRUSION INSTRUMENTATION HAVING BI-DIRECTIONAL COEFFICIENT OF SURFACE FRICTION WITH BODY TISSUE

(75) Inventor: Boris Reydel, West Caldwell, NJ (US)

(73) Assignee: Wilson-Cook Medical Incorporated, Winston-Salem, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,331

(22) Filed: Nov. 2, 1998

(65) Prior Publication Data

US 2002/0156454 A1 Oct. 24, 2002

Related U.S. Application Data

(63) Continuation-in-part of application No. 08/989,413, filed on Dec. 12, 1997, now abandoned.

(51) Int. Cl.[7] .................................................. A61M 5/32
(52) U.S. Cl. .......................... 604/175; 604/264; 604/523; 600/585
(58) Field of Search .............................. 604/174, 175, 604/264, 270, 523; 606/191, 197; 623/1.1, 1.11, 1.22; 600/129, 139, 585, 433, 435, 114, 121, 124

(56) References Cited

U.S. PATENT DOCUMENTS

| 3,635,223 | A | * | 1/1972 | Klieman ..................... 128/348 |
| 3,665,928 | A | * | 5/1972 | Del Guercio ............ 604/95.03 |
| 3,938,529 | A |   | 2/1976 | Gibbons ..................... 128/349 |
| 4,207,872 | A | * | 6/1980 | Meiri et al. .............. 254/134.6 |
| 4,592,341 | A | * | 6/1986 | Omagari et al. ................ 128/4 |
| 4,959,057 | A | * | 9/1990 | Lang .......................... 604/264 |
| 5,009,659 | A | * | 4/1991 | Hamlin et al. .............. 606/159 |
| 5,336,164 | A | * | 8/1994 | Snider et al. .................. 604/4 |
| 5,454,364 | A | * | 10/1995 | Kruger ....................... 600/114 |
| 5,551,443 | A | * | 9/1996 | Sepetka et al. ............. 128/772 |
| 5,762,631 | A | * | 6/1998 | Klein .......................... 604/171 |
| 5,902,285 | A | * | 5/1999 | Kudsk et al. ............... 604/270 |
| 5,984,896 | A | * | 11/1999 | Boyd .......................... 604/175 |
| 6,063,069 | A | * | 5/2000 | Cragg et al. ................ 604/508 |
| 6,106,485 | A | * | 8/2000 | McMahon .................. 600/585 |
| 6,293,907 | B1 |   | 9/2001 | Axon et al. |

FOREIGN PATENT DOCUMENTS

| WO |  9743941 | 11/1997 |
| WO | WO 99/29362 | 6/1999 |
| WO | WO 00/06239 | 2/2000 |
| WO | WO 00/13736 | 3/2000 |
| WO | WO 00/69498 | 11/2000 |

* cited by examiner

Primary Examiner—Brian L. Casler
Assistant Examiner—Cris L. Rodriguez
(74) Attorney, Agent, or Firm—Brinks Hofer Gilson & Lione

(57) ABSTRACT

This invention provides novel instrumentation surface structure for catheters, guide wires and other instrumentation for entering body canals to an internal body work site. This instrumentation is structured with a bi-directional surface friction for engaging tissue within the cavities and canals that they navigate. In this manner the naturally occurring peristalatic contractions are employed to advantageously grasp and carry the instrumentation toward its desired work site, significantly decreasing the risks of puncture and significantly decreasing the surgeon's time for entry of instruments to desired work sites in such procedures as small bowel enteroscopy where an endoscope enters the esophagus to be dynamically moved to work sites in the small intestine or colonoscopy where an endoscope enters the anal canal to be moved through the entire colon and gradually into the terminal ileum.

44 Claims, 3 Drawing Sheets

BODY CANAL INTRUSION INSTRUMENTATION HAVING BI-DIRECTIONAL COEFFICIENT OF SURFACE FRICTION WITH BODY TISSUE

This is a continuation-in-part of my copending application of the same title: Ser. No. 08/989,413 filed Dec. 12, 1997 now abandoned.

TECHNICAL FIELD

This invention relates to instrumentation for invading body canals non-destructively and with a minimum of trauma, and more particularly it relates to the interface between the instruments and body tissue during dynamic ingress and egress of surgical instrumentation into the canals.

BACKGROUND ART

It has been the direction of the prior art to fashion surface structure of instrumentation for non-destructive invasion of body canals with very slippery surface structure to facilitate ingress and this accordingly produces low friction upon egress.

In the parent application, which is incorporated herein in entirety by reference, however it is disclosed that the ingress of the instrumentation into a desired body site has been facilitated by introduction of novel instrumentation surface structure having a bi-directional coefficient of friction with engaged tissue within the cavities and canals that they navigate. In this manner the naturally occurring peristalatic contractions may advantageously grasp and carry the instrumentation toward its desired work site, significantly decreasing the risks of puncture and significantly decreasing the surgeon's time for entry of instruments to desired work sites in such procedures as small bowel enteroscopy where an endoscope enters the esophagus passing through the stomach to be placed at work sites in the small intestine. Greater friction upon egress is supplied by microscopic or macroscopic surface texture that does not discomfort the patient or inflame the interfacing body tissue upon egress.

Thus, it has been discovered that significant advantages are afforded by such improved instrumentation surfaces with differential surface friction upon ingress and egress. Such advantages are realized, for example, in the surgical process of feeding such instrumentation into the tortuous, angulated and loosely fixated structures of the body tissue along the body canals through which the instrumentation must be fed. For example, in the case of small bowel enteroscopy an endoscope is fed from the esophagus and through the stomach into the intestines where the distal end must be manipulated to confront curves and folds in the small intestine and corresponding changes in travel direction. With the bi-directional coefficient of friction provided by this invention, the natural peristaltic waves of the body that carry food through this path are engaged to more easily find and traverse the right path through the stomach and the curves and folds of the intestines. It would be impossible to use the peristaltic waves with the slipperiness of the conventional instrumentation of the prior art which has the same coefficient of friction in ingress and egress directions.

The instrumentation to which this invention is directed comprises catheters, guide wires and medical instruments generally employed for dynamic movement into and out of body canals to internal body work sites, which are also employed at times for inspection of the condition of the canals. The modified instrumentation surfaces of this invention thus function in the dynamic ingress and egress through body canals. Thus, the surface structure is fashioned to expedite dynamic entry and withdrawal as distinguished for example from held in position stents providing the stent device with anchoring barbs resisting egress, typically shown in R. P. Gibbons U.S. Pat. No. 3,938,529, wherein the barbs resist movement of the stent both inwardly and outwardly and to avoid damage to body tissue and discomfort of the patient require for the stent to be confined during insertion and inserted through a cystoscope or like instrument into the work site wherein the barbs firmly engage the body tissue lock the stent into a permanent resident and stationary internal body position.

Accordingly it is an objective of this invention to provide improved medical devices for dynamic entry into work sites along body canals to support corresponding improved surgical methods facilitating the ingress of body intrusion instrumentation to those worksites and egress retrieval therefrom without trauma or inflammation of the canal body tissue interfacing with the inserted instrumentation.

A more specific objective of this invention is to provide preferred embodiments of the instrumentation surface structure provided by this invention with differential surface friction characteristics in the ingress and egress directions of movement of such character that trauma and inflammation of the canal body tissue is avoided during the dynamic movements.

DISCLOSURE OF THE INVENTION

Body invasion instrumentation afforded by this invention for ingress and egress into and out of body canals toward internal work sites must be manipulated with little inflammation and discomfort to body tissue at the interface between the instruments and body tissue during ingress and egress of the instrumentation. For this reason the prior art has introduced ways to make surfaces of such instrumentation slippier to avoid any improved kind of barbs or roughness. However this invention relates explicitly to improved methods of surgical exploration in inserting the instrumentation that reduces the need for probing which could inflame or puncture the canal walls. Thus, the instrumentation counters that trend to make instrumentation surfaces slipperier to the extent of providing modified instrumentation surfaces that have a differential friction upon ingress and egress.

The structure for achieving the differential friction property employs microscopic or macroscopic sized surface texture patterns that may be inserted and removed from internal body worksites with little discomfort or inflammation of interfacing body tissue. The preferred structures provide appropriate non-toxic materials of desirable flexibility to navigate body canals with tortuous and angulated paths thereby to withstand the scrutiny of good medical practice and sterility. The instrumentation includes some throw away after single use instruments such as guide wires and catheters as well as instruments that need to be sterilized and reused such as endoscopes. In general it has been found that certain plastics with treated exterior surfaces for providing bi-directional texture are advantageous, and that removable adhesive tapes or elastic sheaths may be disposably used for endoscopes, for example.

This leads to significantly improved surgical procedures for ingress into a work site deep inside the body. In particular the surgeon can control movement of the instrumentation into the worksite with the help of peristaltic propagation normally exerted by the patient's body. Thus, the differential surface friction feature will cause the instrumentation to naturally flow along the body canals and cavities such as the stomach to navigate desired openings such as the duodenum and small or large intestines, to facilitate movement along tortuous, angulated and loosely fixated body tissue paths. This decreases the possibility of puncture, and saves a considerable amount of the time a surgeon employs in manipulating the instrumentation to an interior body worksite.

Preferred embodiments of producing the bidirectional coefficient of surface friction upon the instrumentation surface are presented with features that facilitate surgical manipulation of the instrumentation and improve the surgeon's proficiency. The instrumentation is of the type including catheters, guide wires or cables, endoscopes and other associated instruments for performing medical and surgical procedures at internal body worksites.

Other features, objects and advantages of this invention will be found throughout the following description and claims and in the appended drawings.

BRIEF DESCRIPTION OF THE DRAWINGS

In the accompanying drawings, wherein like reference characters in the different views relate to similar features to facilitate comparison.

THE PREFERRED EMBODIMENTS

Figure 1:
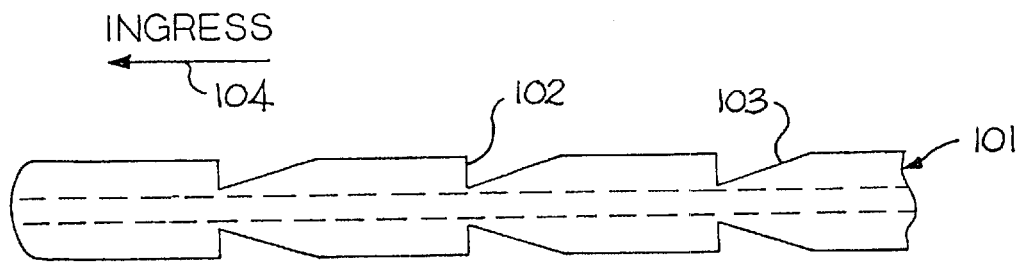
FIG. 1 is a side view sketch of a catheter fragment with a specific surface geometry pattern that provides the bi-directional surface friction in the ingress and egress directions of the catheter which characterizes this invention.

For the surgical procedures described in more detail in the parent application, a line of simply manufactured and thus inexpensive body intrusion instruments encompassing the characteristic bi-directional surface friction surface structure of this invention are herewith disclosed. These structures are thus grasped by the interface body tissue in the canals in which they are inserted employing naturally caused peristaltic wave action, such as swallowing, moving from the stomach into the duodenum or movement along the intestinal tract, for facilitating ingress in view of a relatively impeding surface friction characteristic in the egress direction. For example, significant advantages are thus afforded in the art of small bowel enteroscopy where the instruments are inserted into the esophagus for moving to a work site in the small intestine. These advantages include less time for the insertion process and deeper insertion with a smaller chance of puncture or trauma to the interfacing canal body tissue.

In general the differential surface friction characteristics may be imparted in several ways, such as directionally roughening the surface by embossing, engraving, molding, brushing, tapering, wrapping or overlapping layers to expose edges, or selectively decreasing friction in one direction on suitable surface structure by lubrication, as will be more fully described hereinafter with respect to different embodiments of the invention. Furthermore some of the embodiments favor rotation of the instrumentation as it dynamically moves in and out of the body canal. For example, a spiral pattern of surface texture may favor rotation by the surgeon during ingress and egress of an instrument, or a guy wire may be fed through a catheter tube as facilitated by internal catheter screw-like structure that automatically rotates the guy wires as they are longitudinally moved into or out of a work site. The rotation feature is particularly important in order to navigate the tortuous and angulated ingress paths along the body canals and to distinguish loosely fixated body tissue at the interface with the distal end of the instrument.

The texture of the surface structure providing the differential in friction for ingress and egress of the instrumentation in general may fall into a range from microscopic to macroscopic. However the frictional surface texture is not barbed nor sized large enough to cause discomfort to a patient or inflammation to the interfacing body tissue in the canals. In that respect the scale of the following embodiments is in general exaggerated in order to show the preferred structural texture pattern details. In general the plastics and/or metallic basic materials, films and adhesives that pass the sterility and compatibility requirements for guide wires, catheters and instrumentation for surgical intrusion into the body canals and provide the appropriate elasticity and rigidity are well known in the present state of the art, and this invention is directed to the feature of obtaining its characteristic bi-directional surface friction advantages.

Figure 2:
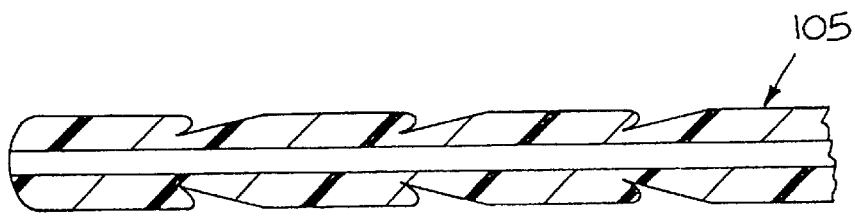
FIGS. 2 and 3 are section views of further catheter embodiment fragments of the invention identifying different surface geometry patterns.
Figure 3:
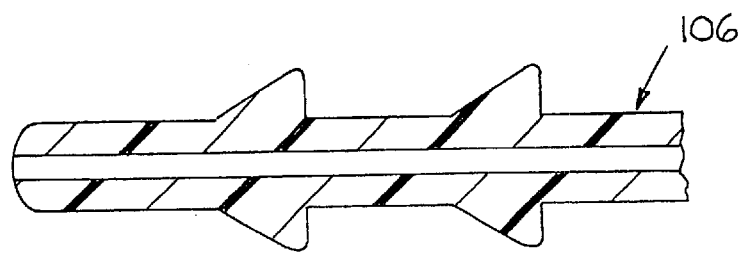

As seen in FIG. 1, the surface texture of a cylindrical catheter 101 may be milled, cast or otherwise deformed to produce the ridges 102 and tapers 103 which provide a differential friction for movement in the ingress direction 104 and the opposing egress direction. These instruments being modified are typically the conventional cylindrical plastic bodies now available in the art. FIGS. 2 and 3 show different surface texture patterns for corresponding catheters 105 and 106. Also in FIG. 1, there is a progressive decrease in the height of the ridges creating a tapering of bi-directional friction.

Figure 4:
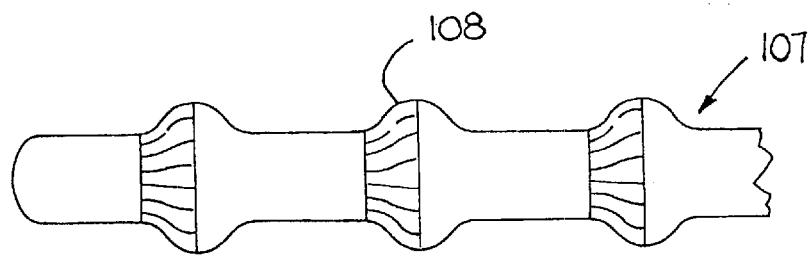
FIG. 4 is a side view sketch of a further catheter fragment embodiment of the invention providing bi-directional friction by selective application of a lubricant surface such as a hydrophilic plastic coating.
Figure 5:
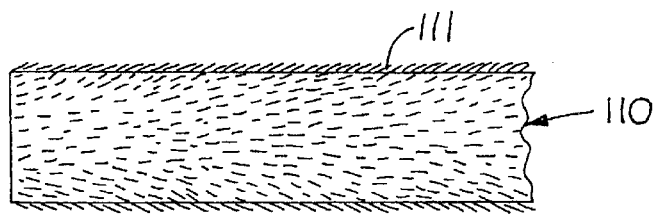
FIG. 5 is a side view sketch of a removable plastic sleeve embodiment of the invention that may envelop an endoscope, for example.

As seen from the FIG. 4 catheter 107, the bi-directional friction differential is established by a hydrophylic polymer coating 108 on the ingress side of the bulbeous protrusions formed in the catheter body. This polymer coating on catheter, as well known in the art makes the coated surface of the catheter slipperier. In the embodiment of FIG. 5, the sheath 110 employs a bi-directional surface texture 111, which may be obtained for example by brushing or milling the surface of a polymer such as polyiden to give the generally macroscopic bi-directional characteristic.

In general at least part of the instrumentation afforded by this invention is inexpensive and may be disposable, such as catheters or guide wires dedicated to a single exploratory use before discarding. However if a reusable instrument such as an endoscope used for colonoscopy is employed the nature of the surface texture need be either disposable as a separate unit or of a nature that is readily cleaned and sterilized after use. Thus, the FIG. 5 sheath 110 represents an elastic condom-like disposable surface cover for the endoscope that imparts the bi-directional differential friction characteristic unique to this invention.

Figure 6:
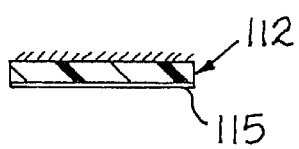
FIGS. 6 to 8 are different section view fragments of adhesive plastic film embodiments of the invention having different surface geometry patterns.
Figure 7:
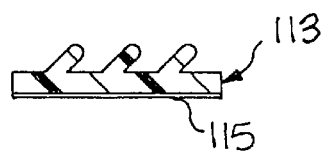
Figure 8:
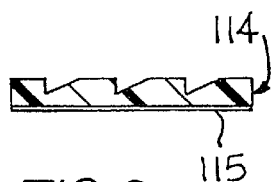

The invention also may be characterized by adhesively applied and therefore disposable surface structure represented by the various surface films 112, 113, 114 of respective FIGS. 6–8, having in common an adhesive coating 115 adapted to retain the bi-directional surface film removably upon the outer surface of a conventional bodily intrusion instrument. These films may be of a surface modified version of a thin semi-stretchable plastic.

Figure 9:
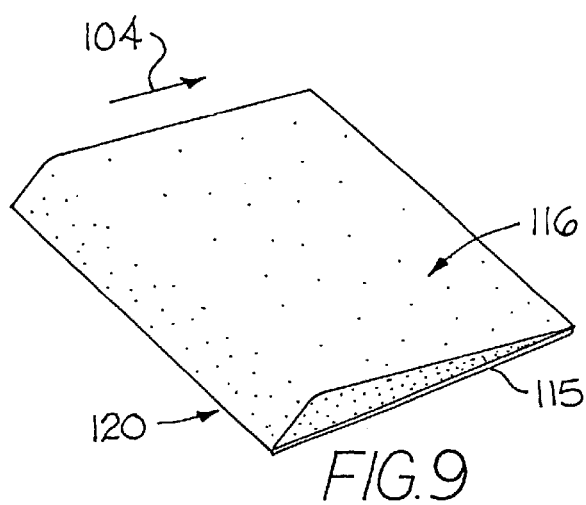
FIG. 9 is a perspective view of a section of adhesive film embodiment of the invention, with a tapered cross section configuration contributing to the bi-directional friction characteristics upon ingress and egress.
Figure 10:
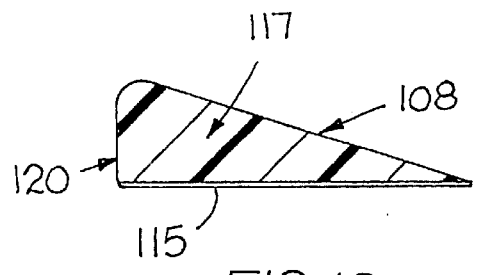
FIG. 10 is an end view in section of another tapered adhesive film embodiment of the invention.
Figure 11:
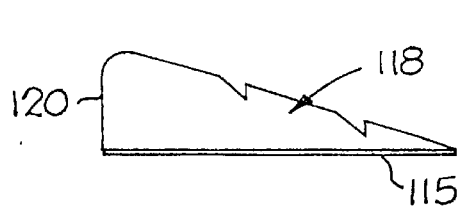
FIGS. 11 and 12 are end view sketches of further tapered adhesive film embodiments of the invention.
Figure 12:
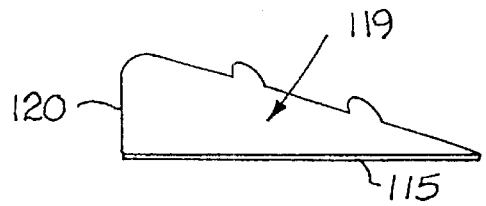

As seen from the respective embodiments 116–119 of FIGS. 9–12, the body of the film strips shown may be tapered. As shown in FIG. 9, ingress is facilitated and egress is impeded by the trailing ridge structure 120. Additionally as shown in FIG. 10 the upper tapered surface may be coated with a lubricant surface 108, or may also contain surface textures as shown in FIGS. 11 and 12 which produce greater differential coefficients of friction in the ingress and egress directions.

Figure 13:
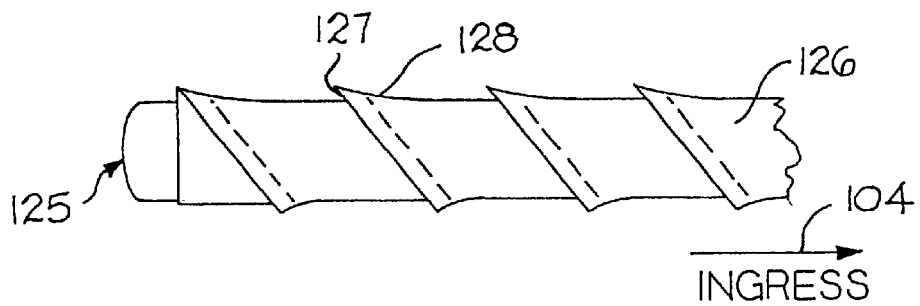
FIGS. 13 and 14 are side view sketches of further embodiments of the invention with surface geometry patterns disposed in spiral patterns along the ingress-egress axis of the instrumentation.
Figure 14:
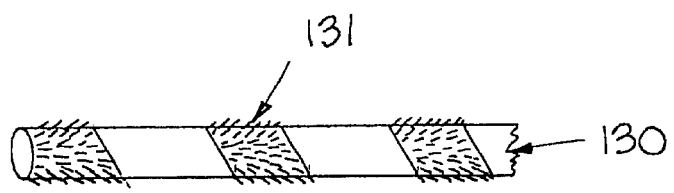

In the FIG. 13 embodiment, the instrument embodiment 125 has a film strip 126 spiral wrapped in an overlapping fashion to provide at the overlapped ridge 127, which together with its tapered trailing edge 128 embody a frictional component that produces a bi-directional surface friction characteristic in the ingress and egress directions. This spiral ridge 127 also provides structure for aiding the surgeon to rotate the instrument 125 in opposite directions that respectively aid the ingress and egress of the instrument from a body cavity. The embodiment 130 of FIG. 14 provides the spiral wrapping feature with the non-overlapped spiral pattern of the adhesive film strip 131 provided with a bi-directional surface texture pattern.

Figure 15:
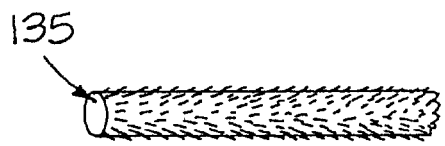
FIG. 15 is a side view sketch of a section of guide wire embodying the invention.
Figure 16:
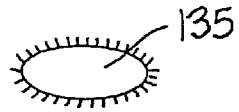
FIG. 16 is an end view sketch of an oval shaped guide wire section of a further embodiment of the invention.
Figure 17:
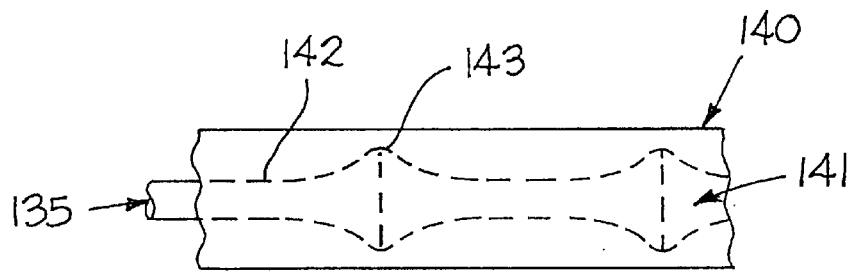
FIG. 17 is a side view sketch illustrating an embodiment of the invention with an oval guide wire within a catheter having mating screw threads arranged in a spiral configuration for automatically rotating the oval guide wire as it advances through the catheter.

FIG. 15 represents guide wire embodiment 135 of the invention, which as seen from the end view of FIG. 16 is preferably of oval shaped cross section. This feature, as illustrated by FIG. 17, wherein the catheter 140 has internal screw-like threads, internally rotates the oval shape guy wire 135 automatically as it progresses from its minor axis position 142 to its major axis position 143.

It is therefore seen that this invention provides various embodiments of the bi-directional surface structure of this invention, which embodiments are adaptable to a wide range of applications in different body canals for unexpectedly saving the surgeon's time and reducing the risks of body tissue damage with inexpensive adaptations of the body intrusion instrumentation with bi-directional coefficients of friction in the ingress and egress directions characteristic of this invention.

Accordingly those features of novelty encompassing the spirit and nature of this invention are defined with particularity in the appended claims.

What is claimed is:

1. A medical device controllable from outside a subject's body for movement into the gastrointestinal tract and removal therefrom, the device comprising:

an elongated member having a diameter sufficiently large to engage walls of the gastrointestinal tract; and an external surface structure disposed about the outer surface of the elongate member and configured to facilitate ingress of the device through the gastrointestinal tract in response to an antegrade peristaltic wave, the external surface structure including a first coefficient of friction which is encountered by the walls of the gastrointestinal tract during the ingress of the device relative to the walls of the gastrointestinal tract, and a second coefficient of friction which is encountered by the walls of the gastrointestinal tract during egress of the device relative to the walls of the gastrointestinal tract, the second coefficient of friction being larger than the first coefficient of friction, wherein said second coefficient is sufficiently large to cause ingress of the elongate member by permitting the elongate member to be carried through the gastrointestinal tract by the antegrade peristaltic wave, wherein said first coefficient of friction is sufficiently small so as to not inhibit ingress of the elongate member in response to the antegrade peristaltic wave, wherein said second coefficient is sufficiently small to prevent the elongate member from causing trauma to the walls of the gastrointestinal tract during egress and removal of the elongate member, and wherein said surface structure comprises a removable surface structure retained upon said device.

2. The device defined in claim 1 wherein said first and second coefficients of friction favor ingress into the gastrointestinal tract and impedes egress upon withdrawal from the gastrointestinal tract.

3. The device defined in claim 1 wherein said surface structure comprises microscopically textured surface topography.

4. The device defined in claim 1 wherein said surface structure comprises macroscopically textured surface topography.

5. The device defined in claim 1 wherein said removable surface structure comprises a plastic film adhesively attached to an outer surface of said device.

6. The device defined in claim 1 wherein the removable surface structure comprises an elastically mounted condom-like sheath covering a portion of an outer surface of the device.

7. The device of claim 1 wherein the device comprises an endoscope.

8. The device of claim 1 wherein said surface structure is a plastic material surface treated to provide said first and second coefficients of friction.

9. The device of claim 1 wherein said surface structure is substantially continuous along a portion of length of the device to be inserted in a particular body canal to reach a work site.

10. The device of claim 1 wherein said surface structure is distributed along at least a distal end portion of the device that is to be inserted in a particular body canal to an internal temporary work site and subsequently withdrawn therefrom.

11. The device of claim 1 which is adapted to be inserted into a particular body canal to an internal temporary work site and subsequently withdrawn therefrom, wherein said surface structure is structured to progressively taper the coefficient of bi-directional surface friction from a distal end toward a proximal end of the device.

12. The device of claim 1 comprising a hollow catheter.

13. The device of claim 1 wherein the device has a protruding surface geometry pattern with the differential friction characteristic embodied in a slippery hydrophilic surface coating on an ingress facing of geometry pattern protrusions.

14. A medical device controllable from outside a subject's body for movement into the gastrointestinal tract and removal therefrom, the device comprising:
   an elongated member having a diameter sufficiently large to engage walls of the gastrointestinal tract; and
   an external surface structure disposed about the outer surface of the elongate member and configured to facilitate ingress of the device through the gastrointestinal tract in response to an antegrade peristaltic wave, the external surface structure including a first coefficient of friction which is encountered by the walls of the gastrointestinal tract during the ingress of the device relative to the walls of the gastrointestinal tract, and a second coefficient of friction which is encountered by the walls of the gastrointestinal tract during egress of the device relative to the walls of the gastrointestinal tract, the second coefficient of friction being larger than the first coefficient of friction,
   wherein said second coefficient is sufficiently large to cause ingress of the elongate member by permitting the elongate member to be carried through the gastrointestinal tract by the antegrade peristaltic wave,
   wherein said first coefficient of friction is sufficiently small so as to not inhibit ingress of the elongate member in response to the antegrade peristaltic wave,
   wherein said second coefficient is sufficiently small to prevent the elongate member from causing trauma to the walls of the gastrointestinal tract during egress and removal of the elongate member, and
   wherein the surface structure comprises adhesive tape adhered to said device.

15. The device defined in claim 14 wherein the tape is a spiral wound strip overlapping to produce a ridge favoring ingress to egress.

16. The device defined in claim 14 wherein the strip of tape has a textured surface characteristic that favors ingress over egress.

17. The device defined in claim 14 wherein the strip of adhesive tape has a tapered thickness and is attached to said device without overlapping so that the taper direction favors ingress over egress.

18. The device as defined in claim 17 further comprising a slippery surface agent on the tape surface.

19. The device defined in claim 14 wherein said surface structure comprises microscopically textured surface topography.

20. The device of claim 14 wherein said surface structure comprises macroscopically textured surface topography.

21. The device of claim 14 wherein said device comprises an endoscope.

22. The device of claim 14 wherein said surface structure is substantially continuous along a portion of length of the device to be inserted in a particular body canal to reach a work site.

23. The device of claim 14 wherein said surface structure is distributed along at least a distal end portion of the device that is to be inserted in a particular body canal to an internal temporary work site and subsequently withdrawn therefrom.

24. The device of claim 14 which is adapted to be inserted into a particular body canal to an internal temporary work site and subsequently withdrawn therefrom, wherein said surface structure is structured to progressively taper the coefficient of bi-directional surface friction from a distal end toward a proximal end of the device.

25. The device of claim 14 comprising a hollow catheter.

26. A medical device controllable from outside a subject's body for movement into the gastrointestinal tract and removal therefrom, the device comprising:
   an elongated member having a diameter sufficiently large to engage walls of the gastrointestinal tract; and
   an external surface structure disposed about the outer surface of the elongate member and configured to facilitate ingress of the device through the gastrointestinal tract in response to an antegrade peristaltic wave, the external surface structure including a first coefficient of friction which is encountered by the walls of the gastrointestinal tract during the ingress of the device relative to the walls of the gastrointestinal tract, and a second coefficient of friction which is encountered by the walls of the gastrointestinal tract during egress of the device relative to the walls of the gastrointestinal tract, the second coefficient of friction being larger than the first coefficient of friction,
   wherein said second coefficient is sufficiently large to cause ingress of the elongate member by permitting the elongate member to be carried through the gastrointestinal tract by the antegrade peristaltic wave,
   wherein said first coefficient of friction is sufficiently small so as to not inhibit ingress of the elongate member in response to the antegrade peristaltic wave,
   wherein said second coefficient is sufficiently small to prevent the elongate member from causing trauma to the walls of the gastrointestinal tract during egress and removal of the elongate member, and
   wherein said device is a guidewire.

27. The device of claim 26 wherein said guidewire is oval in cross section.

28. The device defined in claim 20 wherein said surface structure comprises microscopically textured surface topography.

29. The device of claim 20 wherein said surface structure comprises macroscopically textured surface topography.

30. The device of claim 20 wherein said surface structure is substantially continuous along a portion of length of the device to be inserted in a particular body canal to reach a work site.

31. The device of claim 20 wherein said surface structure is distributed along at least a distal end portion of the device that is to be inserted in a particular body canal to an internal temporary work site and subsequently withdrawn therefrom.

32. The device of claim 20 which is adapted to be inserted into a particular body canal to an internal temporary work site and subsequently withdrawn therefrom, wherein said surface structure is structured to progressively taper the coefficient of bi-directional surface friction from a distal end toward a proximal end of the device.

33. A medical device controllable from outside a subject's body for movement into the gastrointestinal tract and removal therefrom, the device comprising:
   an elongated member having a diameter sufficiently large to engage walls of the gastrointestinal tract; and
   an external surface structure disposed about the outer surface of the elongate member and configured to facilitate ingress of the device through the gastrointestinal tract in response to an antegrade peristaltic wave, the external surface structure including a first coefficient of friction which is encountered by the walls of the gastrointestinal tract during the ingress of the device relative to the walls of the gastrointestinal tract, and a second coefficient of friction which is encountered by the walls of the gastrointestinal tract during egress of the device relative to the walls of the gastrointestinal tract, the second coefficient of friction being larger than the first coefficient of friction, wherein said second coefficient is sufficiently large to cause ingress of the elongate member by permitting the elongate member to be carried through the gastrointestinal tract by the antegrade peristaltic wave, wherein said first coefficient of friction is sufficiently small so as to not inhibit ingress of the elongate member in response to the antegrade peristaltic wave, wherein said second coefficient is sufficiently small to prevent the elongate member from causing trauma to the walls of the gastrointestinal tract during egress and removal of the elongate member, and wherein said device comprises a hollow catheter, said hollow catheter containing an internal spiral structure adapted to engage and rotate an instrument moved within the hollow catheter.

34. The device of claim 33 wherein said hollow catheter presents an oval cross section for rotating a guidewire having an oval cross section.

35. The device defined in claim 33 wherein said differential friction favors ingress toward the work site and impedes egress upon withdrawal from the work site.

36. The device defined in claim 33 wherein said surface structure comprises microscopically textured surface topography.

37. The device defined in claim 33 wherein said surface structure comprises macroscopically textured surface topography.

38. The device defined in claim 33 wherein said surface structure comprises a removable surface structure retained upon said device.

39. The device defined in claim 33 wherein the surface structure comprises adhesive tape adhered to said device.

40. The device of claim 33 wherein said surface structure is substantially continuous along a portion of length of the device to be inserted in a particular body canal to reach a work site.

41. The device of claim 33 wherein said surface structure is distributed along at least a distal end portion of the device that is to be inserted in a particular body canal to an internal temporary work site and subsequently withdrawn therefrom.

42. The device of claim 33 which is adapted to be inserted into a particular body canal to an internal temporary work site and subsequently withdrawn therefrom, wherein said surface structure is structured to progressively taper the coefficient of bi-directional surface friction from a distal end toward a proximal end of the device.

43. A medical device, providing movement into and removal of the device from a body canal, comprising:

an external canal contacting surface on the device, the external surface further comprising a structure configured so as to facilitate natural ingress of the device resulting from antegrade peristaltic action of the canal during insertion thereof, while permitting atraumatic egress of the device from the canal upon removal therefrom; and wherein the external surface further comprises at least one of a microscopically and macroscopically textured surface topography, and further wherein the external surface further comprises a removable structure disposed thereon.

44. The medical device of claim 43, wherein the removable structure further comprises at least one of a plastic film, sheath, adhesive, and tape.

* * * * *

UNITED STATES PATENT AND TRADEMARK OFFICE
CERTIFICATE OF CORRECTION

PATENT NO. : 6,589,213 B2  Page 1 of 1
DATED : July 8, 2003
INVENTOR(S) : Boris Reydel It is certified that error appears in the above-identified patent and that said Letters Patent is hereby corrected as shown below:

Title page,
Item [56], References Cited, U.S. PATENT DOCUMENTS, insert the following:
-- 3,938,529  2/1976  Gibbons
   4,465,072  8/1984  Taheri
   5,059,169  10/1991  Zilber
   5,092,348  3/1992  Dubrul et al.
   5,693,014  12/1997  Abele et al. --.
FOREIGN PATENT DOCUMENTS, insert the following:
-- 9833469  8/1998  WIPO --.

Column 8,
Lines 41, 44, 46, 50 and 54, delete "claim 20" and substitute -- claim 26 -- in its place.

Signed and Sealed this

Sixth Day of July, 2004

JON W. DUDAS
*Acting Director of the United States Patent and Trademark Office*